United States Patent
Chen

(10) Patent No.: US 11,573,164 B2
(45) Date of Patent: Feb. 7, 2023

(54) METHODS OF DETERMINING CATION EXCHANGE SITES OCCUPIED BY CRUDE OIL AND THE WETTABILITY OF CATION EXCHANGE SITES IN ROCK CORE SAMPLES IN A PRESERVED STATE

(71) Applicant: SAUDI ARABIAN OIL COMPANY, Dhahran (SA)

(72) Inventor: Quan Chen, Al Khobar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 466 days.

(21) Appl. No.: 16/858,989

(22) Filed: Apr. 27, 2020

(65) Prior Publication Data

US 2021/0333188 A1 Oct. 28, 2021

(51) Int. Cl.
- *G01N 33/24* (2006.01)
- *G01N 30/96* (2006.01)
- *G01N 13/00* (2006.01)

(52) U.S. Cl.
CPC ............. *G01N 13/00* (2013.01); *G01N 30/96* (2013.01); *G01N 33/241* (2013.01)

(58) Field of Classification Search
CPC ....... G01N 33/241; G01N 30/96; G01N 13/00
(Continued)

(56) References Cited

U.S. PATENT DOCUMENTS

| | | | | |
|---|---|---|---|---|
| 4,074,755 A | * | 2/1978 | Hill | E21B 43/16 166/252.1 |
| 11,300,494 B2 | * | 4/2022 | Chen | G01N 15/082 |

(Continued)

FOREIGN PATENT DOCUMENTS

WO 2016/105395 A1 6/2016

OTHER PUBLICATIONS

Borazjani, S. et al., "Ion-Exchange Inverse Problem for Low-Salinity Coreflooding", Transport in Porous Media, Spring Nature B.V., vol. 128, Mar. 2019, pp. 571-611 (41 pages).
(Continued)

*Primary Examiner* — Arlen Soderquist
(74) *Attorney, Agent, or Firm* — Osha Bergman Watanabe & Burton LLP

(57) ABSTRACT

A method for determining properties of different cation exchange sites in a rock core sample, at a preserved state of the rock core sample may include providing a rock core sample that includes a plurality of indigenous exchangeable cations adsorbed onto the cation exchange sites, a plurality of cation exchange sites occupied by a crude oil, and one or more fluids occupying pore spaces in the rock core sample; subjecting the rock core sample to a plurality of coreflooding steps, the plurality of coreflooding step displacing the plurality of indigenous exchangeable cations, the crude oil, and the one or more fluids in at least three separate coreflooding steps to render the rock core sample clean of native components; determining an amount of indigenous exchangeable cations adsorbed onto the cation exchange sites; subjecting the rock core sample clean of native components to a plurality of coreflooding steps to determine a total amount of exchangeable cations adsorbed onto the cation exchange sites when the rock core sample is clean of native components; and determining at least one property of different cation exchange sites in the rock core sample at the preserved state based on the amount of indigenous exchangeable cations and the total amount of exchangeable cations.

21 Claims, 5 Drawing Sheets

(58) Field of Classification Search
USPC .......................................................... 436/31
See application file for complete search history.

(56) References Cited

U.S. PATENT DOCUMENTS

| | | | |
|---|---|---|---|
| 2007/0246649 A1* | 10/2007 | Jacobi | G01V 5/12 |
| | | | 250/269.6 |
| 2012/0192640 A1 | 8/2012 | Minh et al. | |
| 2013/0057277 A1 | 3/2013 | Zielinski et al. | |
| 2013/0125630 A1 | 5/2013 | Collins et al. | |
| 2013/0248251 A1* | 9/2013 | Kulkarni | E21B 21/06 |
| | | | 703/2 |
| 2014/0196902 A1* | 7/2014 | Southwick | E21B 43/16 |
| | | | 507/224 |
| 2014/0224482 A1 | 8/2014 | Grayson et al. | |
| 2014/0345862 A1 | 11/2014 | Jerauld et al. | |
| 2016/0097876 A1* | 4/2016 | Freed | G01V 3/30 |
| | | | 703/2 |
| 2016/0186556 A1* | 6/2016 | Rasmus | G06F 17/11 |
| | | | 703/2 |
| 2017/0017011 A1 | 1/2017 | Howard et al. | |
| 2017/0030819 A1 | 2/2017 | Mccarty et al. | |
| 2018/0100942 A1* | 4/2018 | Zhang | G01V 3/10 |
| 2019/0094120 A1* | 3/2019 | Gmira | G01N 15/082 |
| 2021/0123877 A1* | 4/2021 | Abdallah | G01N 27/221 |
| 2021/0124079 A1* | 4/2021 | Ma | G01V 3/28 |
| 2021/0333191 A1* | 10/2021 | Chen | G01N 33/241 |
| 2021/0333258 A1* | 10/2021 | Chen | G01N 33/241 |

OTHER PUBLICATIONS

Nasralla, Ramez A. and Hisham A. Nasr-El-Din, "Journal of Petroleum Science and Engineering", ScienceDirect, Elsevier B.V., vol. 122, Aug. 2014, pp. 384-395 (12 pages).

International Search Report issued in corresponding International Application No. PCT/US2020/031593, mailed Feb. 16, 2021 (5 pages).

Written Opinion issued in corresponding International Application No. PCT/US2020/031593, dated Feb. 16, 2021 (5 pages).

* cited by examiner

METHODS OF DETERMINING CATION EXCHANGE SITES OCCUPIED BY CRUDE OIL AND THE WETTABILITY OF CATION EXCHANGE SITES IN ROCK CORE SAMPLES IN A PRESERVED STATE

BACKGROUND

A common practice in the oil and gas industry is to inject water into a hydrocarbon reservoir to maintain its pressure and displace hydrocarbons to production wells. This injection of water is commonly referred to as secondary stage injection or secondary recovery. Seawater and aquifer water are some of the more widely used resources for injection. Injection of a second fluid in order to displace additional hydrocarbons after no more hydrocarbons are being extracted using the first fluid is referred to as tertiary stage injection or tertiary recovery. A remaining portion of the initial hydrocarbons in the reservoir can be extracted utilizing expensive enhanced recovery techniques, such as carbon dioxide ($CO_2$) injection or chemical flooding. A relatively more recent technique involves injection of aqueous solutions with modified ionic compositions.

Understanding properties of the hydrocarbon reservoir can assist in optimizing extraction of the stored hydrocarbons from the reservoir. One technique to understand properties of the hydrocarbon reservoir is to develop computer-generated software models of all or portions of the reservoir. To develop such models, a reservoir rock sample from the hydrocarbon reservoir is evaluated and results of the evaluation are provided as an input to the computer software program that generates the software models. The reservoir rock sample can be evaluated by performing one or more of several experiments under laboratory conditions or under reservoir conditions (that is, the conditions experienced by the sample in the hydrocarbon reservoir). Rock wettability, specifically, the wettability of the porous structure within the rock, is one of the parameters of the reservoir rock sample that can be evaluated.

Wettability is the tendency of a fluid to spread across or adhere to a solid surface in the presence of other immiscible fluids. Wettability can describe the preference of a solid to be in contact with one fluid rather than another. In relation to the oil and gas industry, wettability can refer to the interaction between fluids such as hydrocarbons or water and a reservoir rock. The wettability of a reservoir can affect the hydrocarbon extraction process. Because wettability can influence not only the profile of initial hydrocarbon saturation but also the hydrocarbon extraction process, such as water flooding and enhanced oil recovery (EOR) processes. However, conventional wettability measurement methods cannot determine the wettability of different cation exchange sites.

Further, existence of clay in reservoir formations has a great impact on reservoir quality of sandstone facies. Clay minerals have different effects on the characteristics of oil reservoirs such as reduction of effective porosity and permeability or overestimation of water saturation due to the increased conductivity. In addition, the presence of clay causes the instability of some parts of wellbore wall. For these reasons, the study of clays in petroleum related investigations is so vital. Cation exchange capacity (CEC) is one of the parameters that is useful for identifying clays and their physical and chemical properties.

The CEC of a rock sample is often determined by a wet chemistry method. However, the determined cation exchange capacity by a wet chemistry method is not reservoir representative for the following reasons: (1) the rock sample is cleaned to remove any oil in the rock sample, which is not representative of the in-situ reservoir conditions; (2) the rock sample is ground to fine particles. However, excessive grinding will increase the cation exchange capacity by exposing more cation exchange sites than the case at the in-situ reservoir conditions, resulting in the overestimation cation exchange capacity. On the other hand, insufficient grinding will lead to some reservoir representative cation exchange sites not being exposed, resulting in underestimation of the cation exchange capacity; and (3) the determined cation exchange capacity does not identity any reservoir representative exchangeable cations on the exchange sites and which of the sites are occupied by crude oil. Oil adsorbed onto the cation exchange sites may impact the cation exchange capacity. Cation exchange between a rock surface and a brine being flushed therethrough can desorb oil that is adsorbed to the surface, thereby impacting oil recovery efforts from the reservoir.

Accordingly, there exists a continuing need for developments in rock sample analysis to improve the enhanced oil recovery efforts.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for determining properties of different cation exchange sites in a rock core sample, at a preserved state of the rock core sample that includes providing a rock core sample that includes a plurality of indigenous exchangeable cations adsorbed onto the cation exchange sites, a plurality of cation exchange sites occupied by a crude oil, and one or more fluids occupying pore spaces in the rock core sample; subjecting the rock core sample to a plurality of coreflooding steps, the plurality of coreflooding step displacing the plurality of indigenous exchangeable cations, the crude oil, and the one or more fluids in at least three separate coreflooding steps to render the rock core sample clean of native components; determining an amount of indigenous exchangeable cations adsorbed onto the cation exchange sites; subjecting the rock core sample clean of native components to a plurality of coreflooding steps to determine a total amount of exchangeable cations adsorbed onto the cation exchange sites when the rock core sample is clean of native components; and determining at least one property of different cation exchange sites in the rock core sample at the preserved state based on the amount of indigenous exchangeable cations and the total amount of exchangeable cations.

In another aspect, embodiments disclosed herein relate to a method for determining an amount of different cation exchange sites occupied by crude oil in a rock core sample, at a preserved state of the rock core sample that includes providing a rock core sample that includes at least a plurality of indigenous exchangeable cations adsorbed onto the cation exchange sites and a plurality of cation exchange sites occupied by a crude oil; displacing the crude oil in the rock core sample with a formation brine until oil ceases production; displacing an excess of cations present in a plurality of interstitial pore spaces of the rock core sample by using a first organic solvent; displacing the plurality of indigenous exchangeable cations from the cation exchange sites of the rock core sample with a first injection fluid until completion of extraction; displacing the first injection fluid by alternately injecting a second organic solvent and a third organic solvent, wherein the third organic solvent is the last injected; displacing the third organic solvent with the formation brine such that the cations present in the formation brine adsorb onto the cation exchange sites; displacing the cations adsorbed onto the cation exchange sites of the rock core sample with a second injection fluid until completion of extraction; calculating an amount of indigenous exchangeable cations adsorbed onto the cation exchange sites and a total amount of the exchangeable cations adsorbed onto the cation exchange sites; and calculating the amount of the different cation exchange sites occupied by crude oil based on the amount of indigenous exchangeable cations adsorbed onto the cation exchange sites and the total amount of the exchangeable cations adsorbed onto the cation exchange sites.

In yet another aspect, embodiments disclosed herein relate to a method for determining a wettability of different cation exchange sites of a rock sample, at a preserved state of the rock core sample that includes providing a rock core sample that includes at least a plurality of indigenous exchangeable cations adsorbed onto the cation exchange sites and a plurality of cation exchange sites occupied by a crude oil; displacing the crude oil in the rock core sample with a formation brine until oil ceases production; displacing an excess of cations present in a plurality of interstitial pore spaces of the rock core sample by using a first organic solvent; displacing a plurality of indigenous exchangeable cations from the cation exchange sites of the rock core sample with a first injection fluid until completion of extraction; displacing the first injection fluid by alternately injecting a second organic solvent and a third organic solvent, wherein the third organic solvent is the last injected; displacing the third organic solvent with the formation brine such that the cations present in the formation brine adsorb onto the cation exchange sites; displacing the cations adsorbed onto the cation exchange sites of the rock core sample with a second injection fluid until completion of extraction; calculating an amount of indigenous exchangeable cations adsorbed onto the cation exchange sites and a total amount of the exchangeable cations adsorbed onto the cation exchange sites; and calculating the wettability of the different cation exchange sites based on the amount of indigenous exchangeable cations adsorbed onto the cation exchange sites and the total amount of the exchangeable cations adsorbed onto the cation exchange sites.

Other aspects and advantages of the claimed subject matter will be apparent from the following description and the appended claims.

DETAILED DESCRIPTION

Figure 1:
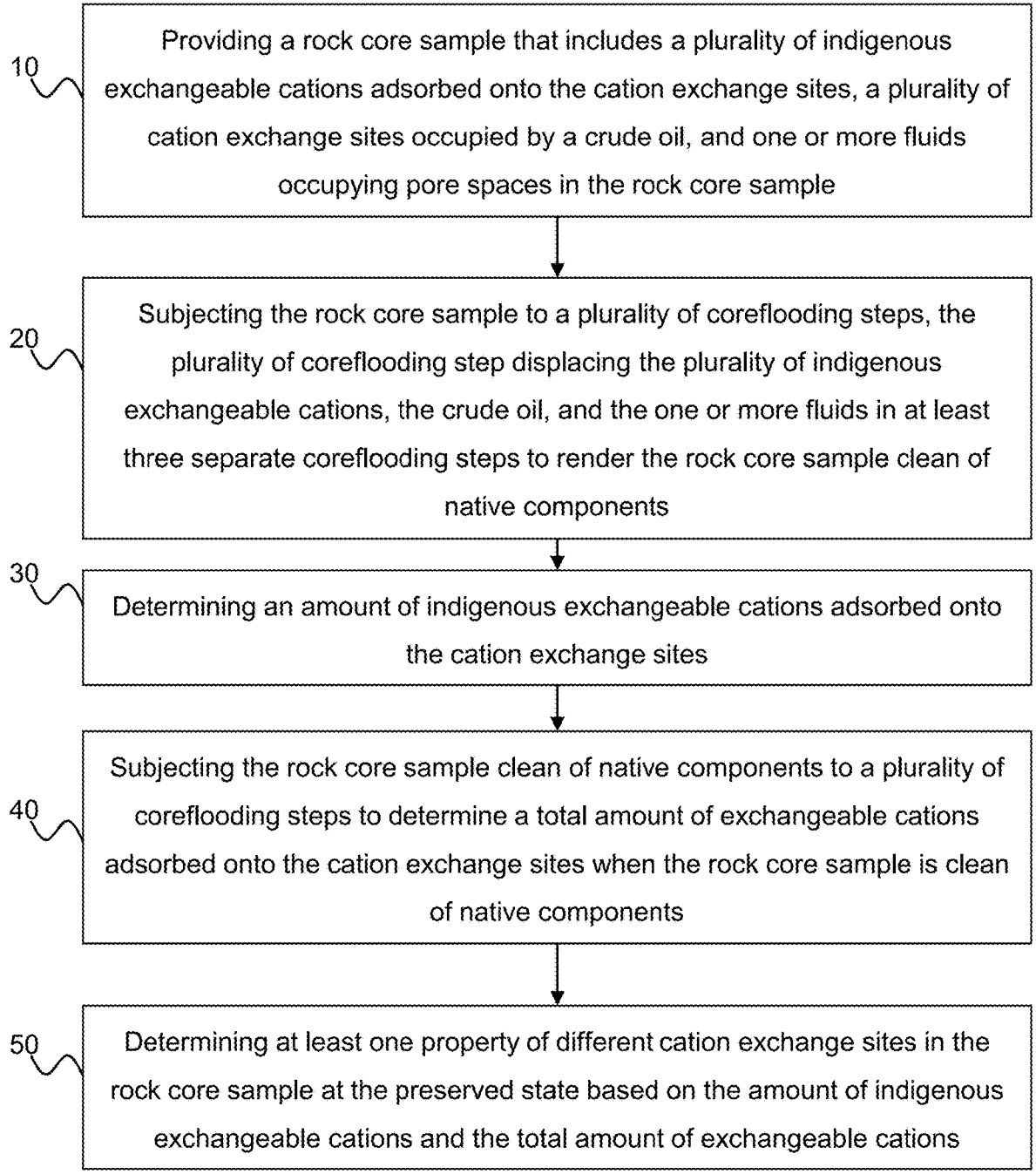
FIG. 1 shows a flow chart according to one or more embodiments of the present disclosure.

In one aspect, embodiments disclosed herein relate to methods of rock sample analysis to provide determinations concerning different cation exchange sites present in the rock core samples. Clay minerals in a reservoir or rock sample have negatively charged sites ($X^-$) on their surfaces which adsorb and hold cations (e.g., $Ca^{2+}$, $Mg^{2+}$, $Na^+$, and $K^+$) by electrostatic force. In particular, the present methods are directed to methodologies that allow for determinations concerning the wettability of different cation exchange sites in a rock core sample and/or different cation exchange site occupied by crude oil, when the rock is in a preserved state (i.e. in the original reservoir condition).

Conventional methods of rock core analysis do not provide for distinctions based on different cation exchange sites, i.e., differentiating between $Ca^{2+}$, $Mg^{2+}$, $Na^+$, and $K^+$, for example. However, in accordance with embodiments of the present disclosure, a rock core sample in a preserved state may be subjected to a series of coreflood steps to provide such differentiation and in particular the wettability of the different sites and which of the different sites are occupied by crude oil. This may advantageously allow for enhanced oil recovery operations to be designed based on such different cation exchange sites and the properties thereof to result in greater efficacy in EOR operations. In particular, such determinations may be made by considering the indigenous exchangeable cations of $Na^+$, $K^+$, $Ca^{2+}$ and $Mg^{2+}$ adsorbed onto cation exchange sites ($[NaX]_e$, $[KX]_e$, $[CaX_2]_e$ and $[MgX_2]_e$) and the total exchangeable cations of $Na^+$, $K^+$, $Ca^{2+}$ and $Mg^{2+}$ adsorbed onto the cation exchange sites, ($[NaX]_T$, $[KX]_T$, $[CaX_2]_T$ and $[MgX_2]_T$). As used herein, the total exchangeable cations adsorbed onto the cation exchange sites refers to when all cation exchange sites are occupied by cations, whereas the indigenous exchangeable cations adsorbed onto the cation exchange sites in the native state in the reservoir. For example, depending on the wettability of the rock surface and the cation exchange sites, in particular, and whether the sites are oil-wet or water-wet, for example, some of the site may be occupied by crude oil, rather than cations. The present methods may determine the wettability of each exchange site and/or the amount of each site occupied by crude oil when the rock sample is in a preserved state. As used herein, when the rock is in a preserved state, it, and specifically the cation exchange sites, is in the original reservoir condition.

As described herein, the present methodology uses coreflooding to sequentially displace native components out of the rock core sample and inject (and displace) replacement fluids therethrough during the analysis. In particular, the present methods separately displace excess components such as fluids (including excess cations) from the pore spaces, then indigenous cations from exchange sites (by replacing the indigenous cations with replacement cations), as well as oil occupying exchange sites. Once the rock core sample is entirely cleaned of all native components, the rock core sample may be filled with cations (of the indigenous type) in order to obtain data concerning the total exchangeable sites (which may be only partially occupied by indigenous cations in the reservoir). Both the indigenous adsorbed cations and the "total" adsorbed cations may be quantified and compared in order to determine the wettability of each exchange site and/or the amount of each site occupied by crude oil.

Such a coreflooding system may include a coreholder, a pumping system, an effluent collection system, a measurement system, as well as temperature and pressure control so that coreflooding experiments may be conducted at conditions mimicking reservoir conditions. Such systems are commercially available. Coreflooding may be utilized on rock types having a permeability of at least 0.1 millidarcy.

Referring now to FIG. 1, a flow chart according to one or more embodiments is shown. As shown, stage 10 may include providing a rock core sample that includes a plurality of indigenous exchangeable cations adsorbed onto the cation exchange sites, a plurality of cation exchange sites occupied by a crude oil, and one or more fluids occupying pore spaces in the rock core sample. Stage 20 may include subjecting the rock core sample to a plurality of coreflooding steps, the plurality of coreflooding step displacing the plurality of indigenous exchangeable cations, the crude oil, and the one or more fluids in at least three separate coreflooding steps to render the rock core sample clean of native components. Stage 30 may include determining an amount of indigenous exchangeable cations adsorbed onto the cation exchange sites. Stage 40 may include subjecting the rock core sample clean of native components to a plurality of coreflooding steps to determine a total amount of exchangeable cations adsorbed onto the cation exchange sites when the rock core sample is clean of native components. Stage 50 may include determining at least one property of different cation exchange sites in the rock core sample at the preserved state based on the amount of indigenous exchangeable cations and the total amount of exchangeable cations.

Figure 2:
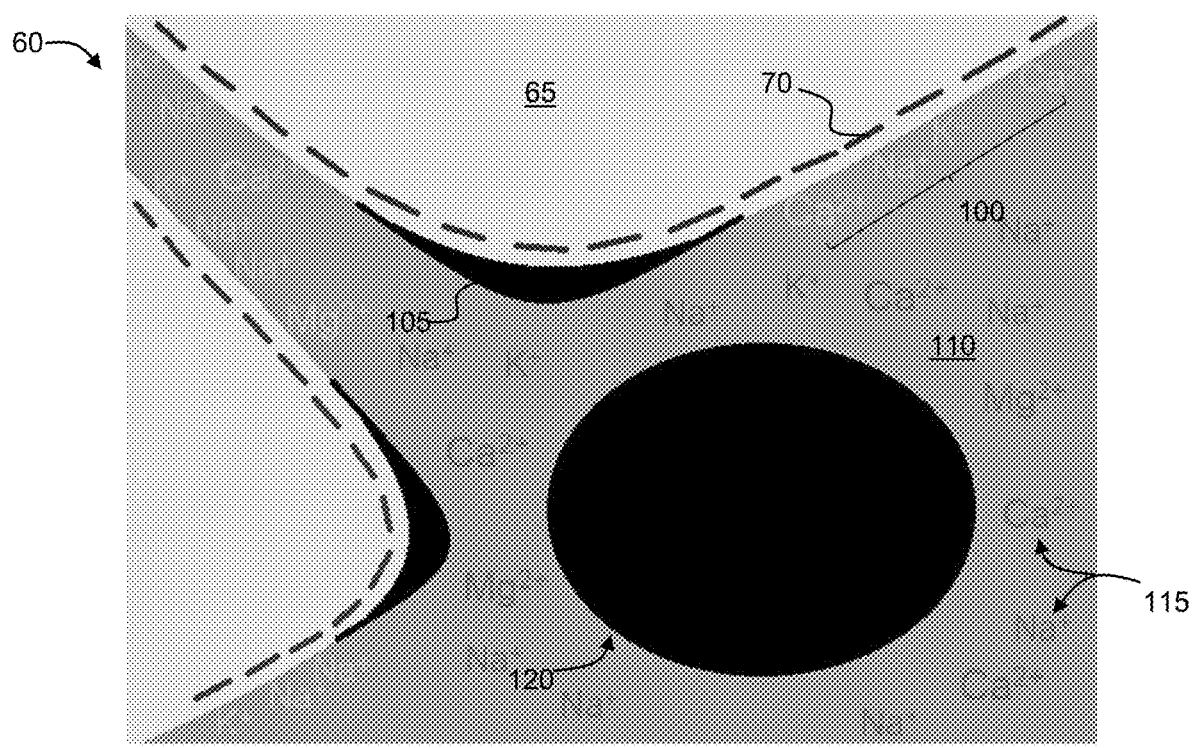
FIGS. 2-8 show schematics of a rock core sample during sequential coreflooding operations in accordance with one or more embodiments of the present disclosure.

FIGS. 2-8 illustrate schematics of a rock core sample during progressive stages of the present coreflooding operations. Initially, the rock core in the preserved state (i.e., in original reservoir conditions, including preserving the cation exchange sites) may be coreflooded with formation brine to displace crude oil from the rock core sample. Formation brine may be injected until oil ceases production from the rock core sample. Referring to FIG. 2, FIG. 2 shows a schematic of a rock core sample 60 following the initial coreflooding with a formation brine. As shown in FIG. 2, rock particles 65 have exchange sites 70 present on the surface thereof. The exchange sites 70 are shown to have some cations 100 and some oil 105 adsorbed thereto. The cations 100 adsorbed onto the exchange sites 70 are referred to as the indigenous exchangeable cations. Otherwise, following the initial coreflooding with a formation brine 110, the pore spaces between the rock particles 65 are occupied by formation brine 110, including an excess of cations 115 (not adsorbed to exchange sites 70) therein. It is also envisioned that some quantity of residual oil 120 may also be present in the pore spaces between rock particles 65.

Figure 3:
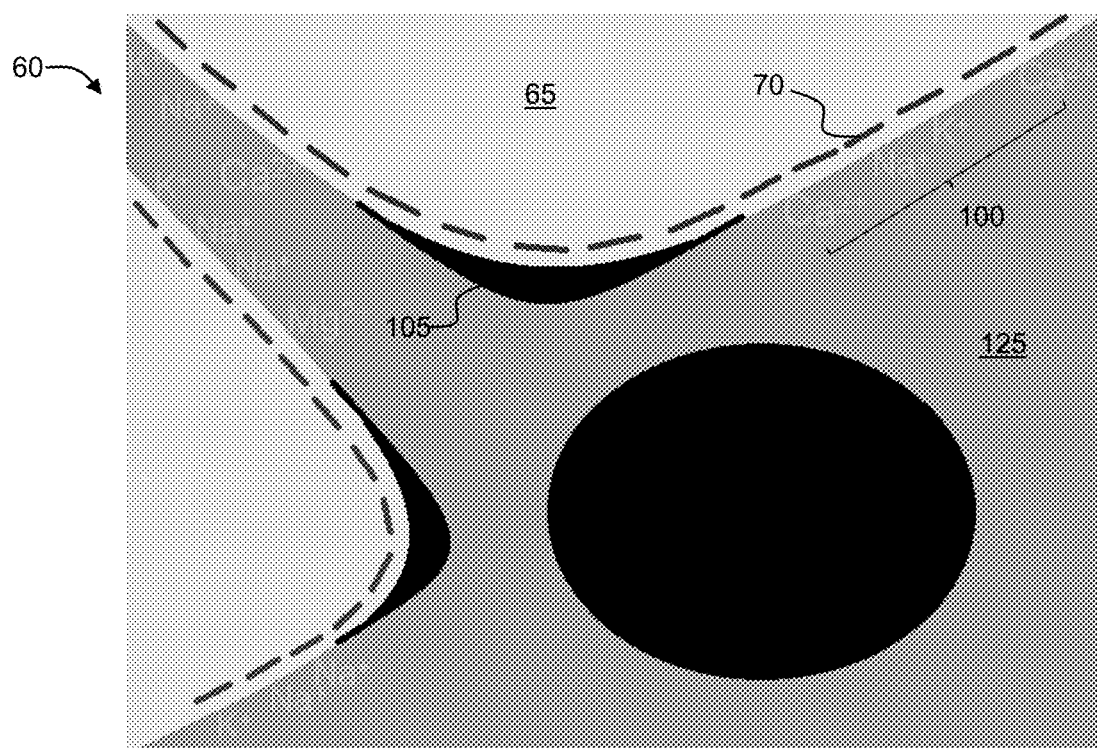

Following the displacement illustrated in FIG. 2, the rock core sample 60 may be coreflooded with an organic solvent, such as but not limited to 95% ethanol, to displace the excess cations 115 (shown in FIG. 2) from the rock core sample 60. To complete the displacement of excess cations 115, a large volume of organic solvent may be used, for example, ranging from an estimated 50 to 80 pore volumes. For the purpose of estimating the volume of organic solvent or other fluid that may be used for the coreflooding, the pore volume may be estimated by measuring the length and diameter and assuming a porosity of 30% for the rock core sample. The effect of such displacement is shown in the schematic illustrated in FIG. 3. As shown in FIG. 3, while the exchange sites 70 still have the cations 100 and oil 105 adsorbed thereto, the pore space between the rock particles 65 is now occupied by organic solvent 125.

Figure 4:
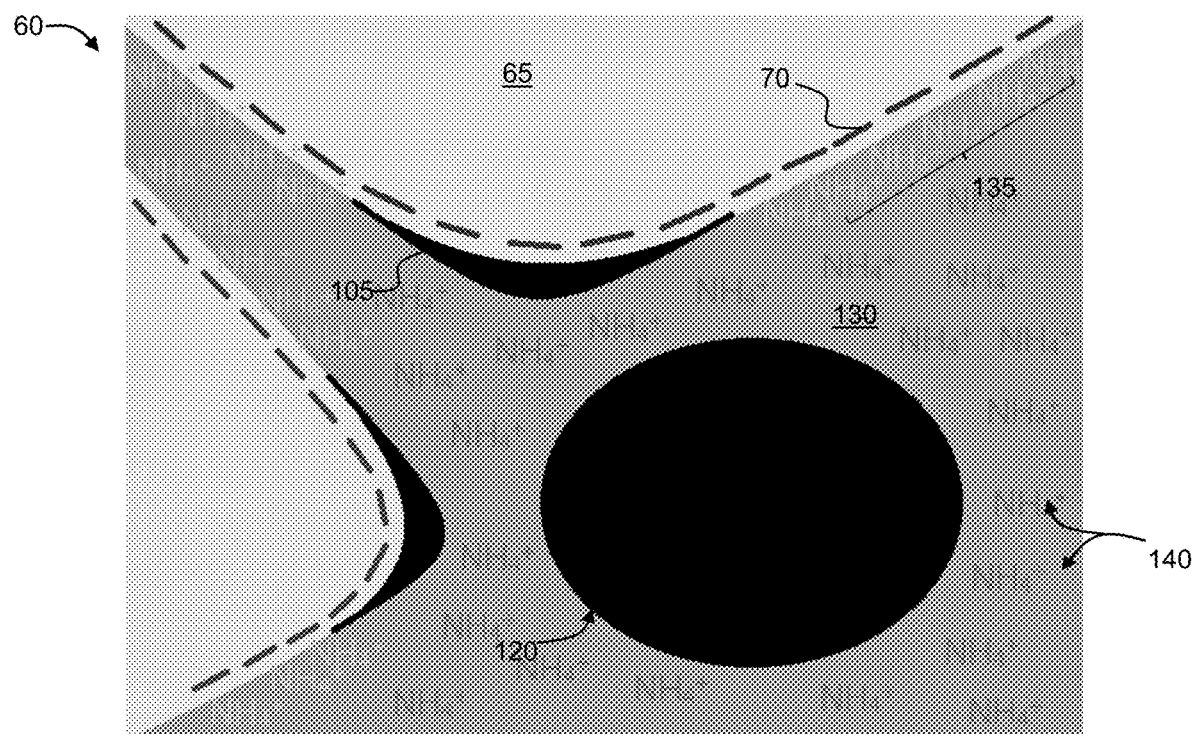

Following the displacement of excess cations, the effect of which is illustrated in FIG. 3, the rock core sample 60 is conducted with an injection fluid to displace the cations 100 (i.e., indigenous exchangeable cations) adsorbed on the exchange sites 70 out of the rock sample 60, the effect of which is illustrated in the schematic shown in FIG. 4. As shown in FIG. 4, following such displacement, in addition to displacing cations (100 in FIG. 3), the organic solvent (125 in FIG. 3) is also displaced from the rock sample 60 such that the pore space between the rock particles 65 is occupied by injection fluid 130 in FIG. 4. Injection fluid 130 may include a replacement cation 135, such as $NH_4^+$ adsorbed onto the exchange sites 70. Additionally, injection fluid 130 may also include excess replacement cations 140 that are not adsorbed onto the exchange sites 70, but which are present in the injection fluid 130. To ensure complete displacement of indigenous exchangeable cations 100, about 50-80 pore volumes of injection fluid 130 may be injected into rock sample 60. In one or more embodiments, the injection fluid 130 may be an ammonium acetate solution, having a concentration ranging from 0.5 to 2.0M and a pH ranging from 7 to 8.5. However, it is envisioned that other injection fluids such a solution of hexaaminecobalt (III) chloride may also be used.

From the extract collected from the coreflooding with the injection fluid, the amount/concentration of the indigenous exchangeable cations (those cations 100 that were originally adsorbed to exchange sites 70, e.g., $Na^+$, $K^+$, $Ca^{2+}$ and $Mg^{2+}$) in the injection fluid extract may be determined by analytical methods, such as but not limited to ion chromatography (IC) specifically cation chromatography, atomic spectroscopic methods such as atomic absorption spectroscopy (AAS), inductively coupled plasma-mass spectrometry (ICP-MS), atomic emission spectrometry (ICP-AES), and optical emission spectrometry (ICP-OES), as well as capillary electrophoresis (CE). In one or more embodiments, the amount of indigenous exchangeable cations may be considered as a mole equivalent per liter of pore volume and represented as $[NaX]_e$, $[KX]_e$, $[CaX_2]_e$, and $[MgX_2]_e$.

Figure 5:
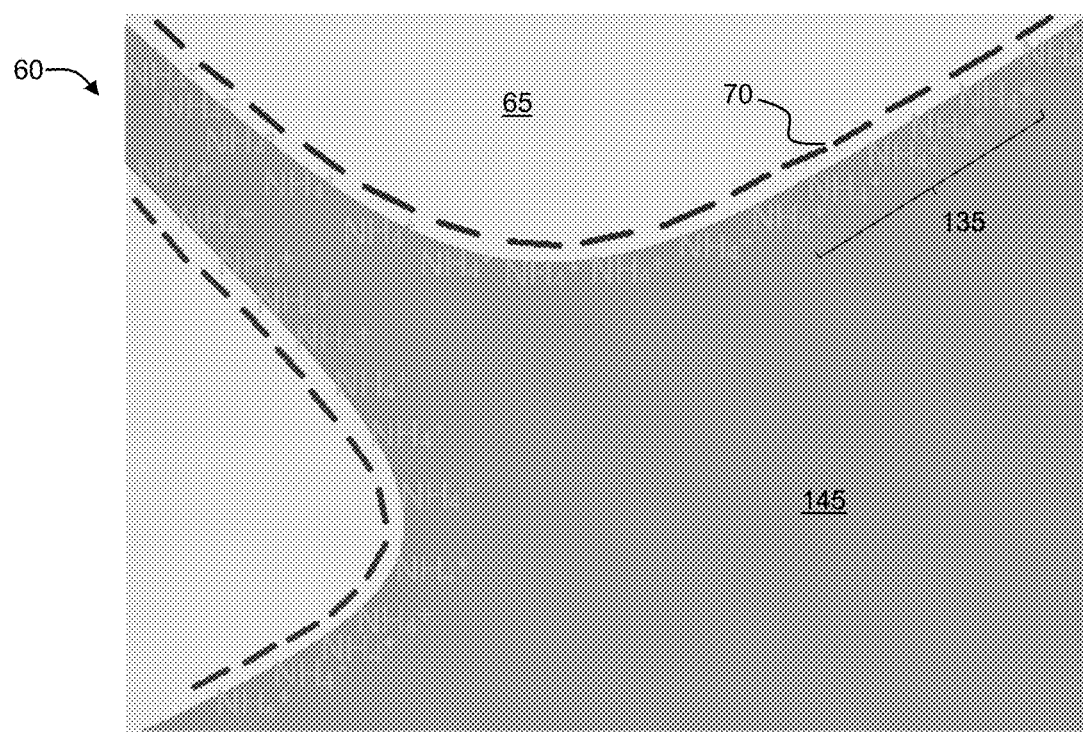

Following the displacement of indigenous exchangeable cations by an injection fluid 130, the rock sample 60 is coreflooded with an alternating sequence of a plurality of organic solvents. Such organic solvents may include at least one solvent that may be effective to remove any residual oil present in the rock core sample 60, including oil 105 adsorbed to the exchange sites 70 as well as residual oil 120 present in the pore spaces. Additionally, the organic solvents may also include at least one solvent that is effective to remove water and salts from the pore space of rock core sample 60. In one or more embodiments, one solvent may be toluene and the other may be methanol. It is envisioned that the solvent miscible in water (e.g., methanol) may be the last organic solvent injected into the rock core sample 60 (such that the water-miscible organic solvent can be completely displaced out of the rock core sample by formation brine as described in the following paragraph). Referring now to FIG. 5, the rock core sample 60, after alternating injection of organic solvents, may have the replacement cations 135 adsorbed to the exchange sites 70, with the pore space being occupied entirely by the water-miscible organic solvent 145. {

Figure 6:
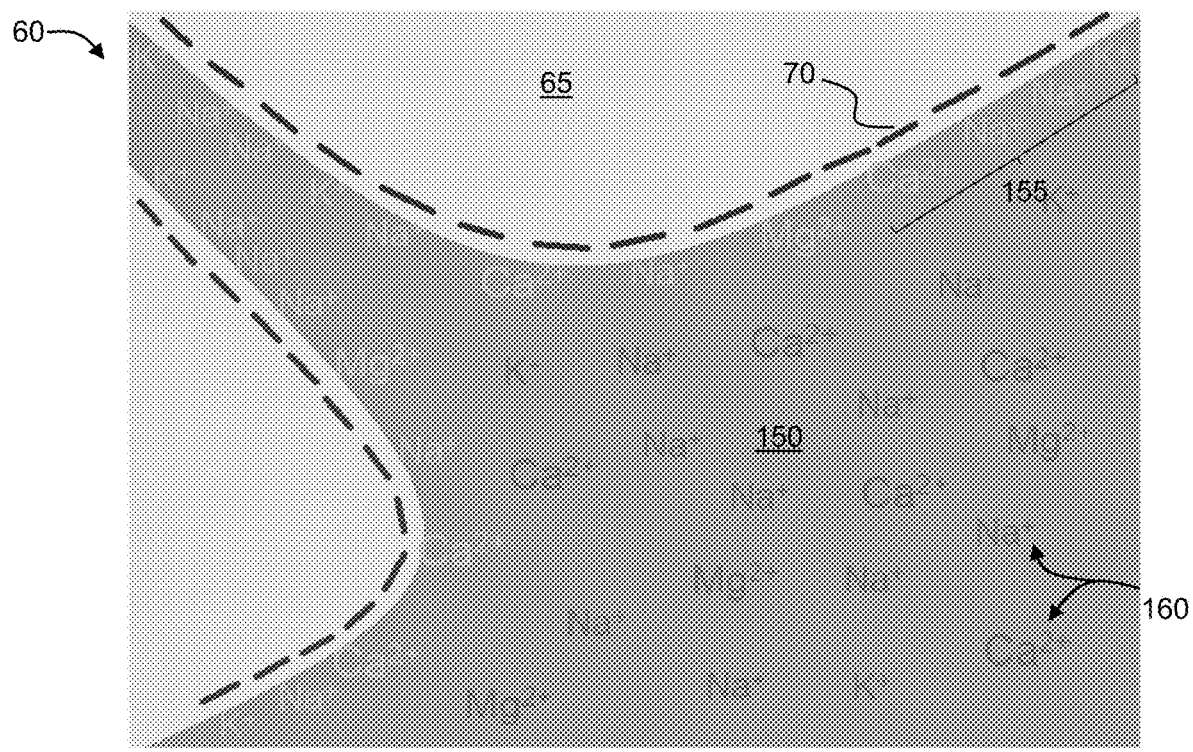

Following the alternating solvent injection, the effect of which is illustrated in FIG. 5, a formation brine may be coreflooded into the rock core sample 60 to displace organic solvent 145 from the rock sample core 60. As shown in FIG. 6, following such displacement, formation brine 150 may be present in the pore spaces between rock particles 65. Formation brine 150 is injected in sufficient volume for complete displacement of organic solvent (145 in FIG. 5). Cations in formation brine exchange with replacement cations 135 such that cations 155 are adsorbed to all exchange sites 70 present on the surface of rock particles 65. Because cations 155 are adsorbed to all exchange sites 70, cations 155 are referred to herein as "total" exchangeable cations 155. Excess cations 160 in formation brine 150 are also present in the pore spaces between rock particles 65. In order to have complete displacement and equilibrium of the exchange sites 70, a large volume of formation brine 150 may be used, for example, ranging from 50 to 80 pore volumes.

In one or more embodiments, the pore volume of the rock core sample 60 may be determined by NMR. Preferably, this determination may be performed as the rock core sample 60 is in a state illustrated in FIG. 6, as the rock core sample 60 contains a single fluid type therein, which may allow for fewer complexities in the NMR determination. The pore volume may be used to quantify the amount of cations relative to the pore volume of the rock core sample 60. However, a NMR analysis performed at another time may account for the presence of more than one fluid, such as a brine and oil.

Figure 7:
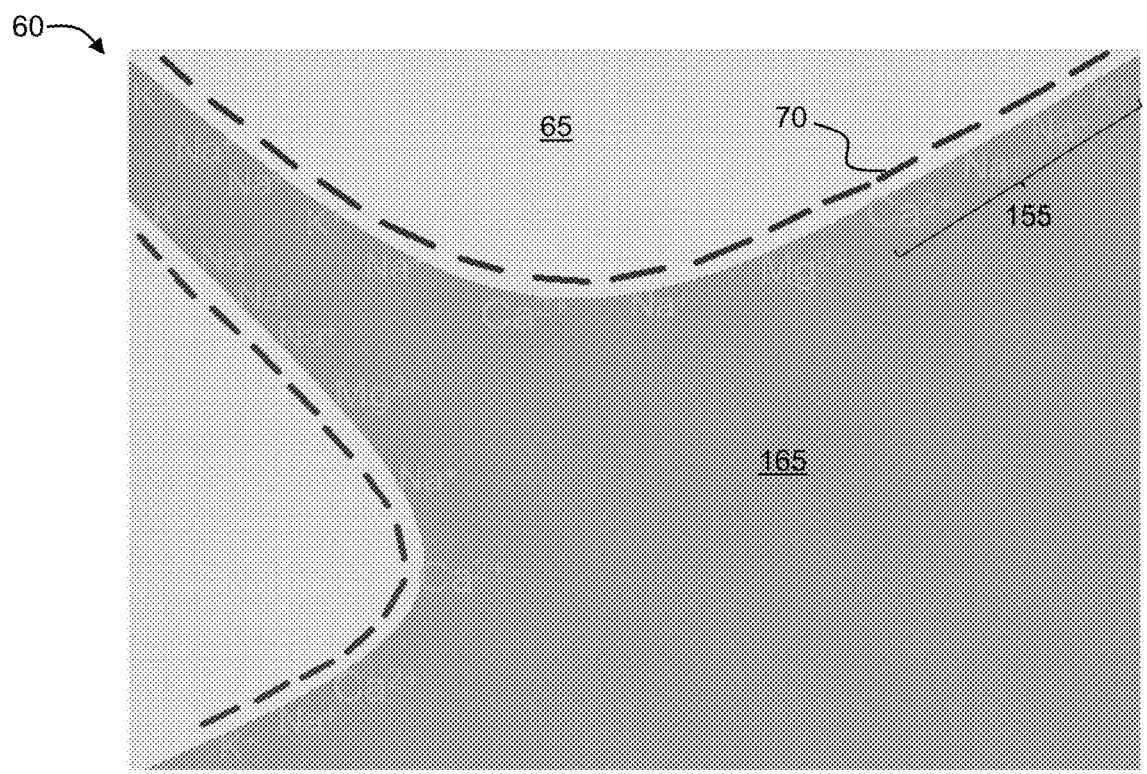

After equilibrating the exchange sites 70 with exchangeable cations 155, the result of which is shown in FIG. 6, the excess cations 160 may be removed from the rock core sample 60. As shown in FIG. 7, excess cations and formation brine (160 and 150, respectively, in FIG. 6) may be displaced from the pore spaces between rock particles 65 by coreflooding the rock sample 60 with an organic solvent, such as but not limited 95% ethanol, to displace the excess cations 160 (shown in FIG. 6) from the rock core sample 60. To complete the displacement of excess cations 160, a large volume of organic solvent may be used, for example, ranging from 50 to 80 pore volumes. The effect of such displacement is shown in the schematic illustrated in FIG. 7. As shown in FIG. 7, while the exchange sites 70 still have the "total" exchangeable cations 155 adsorbed thereto, the pore space between the rock particles 65 is now occupied by organic solvent 165.

Figure 8:
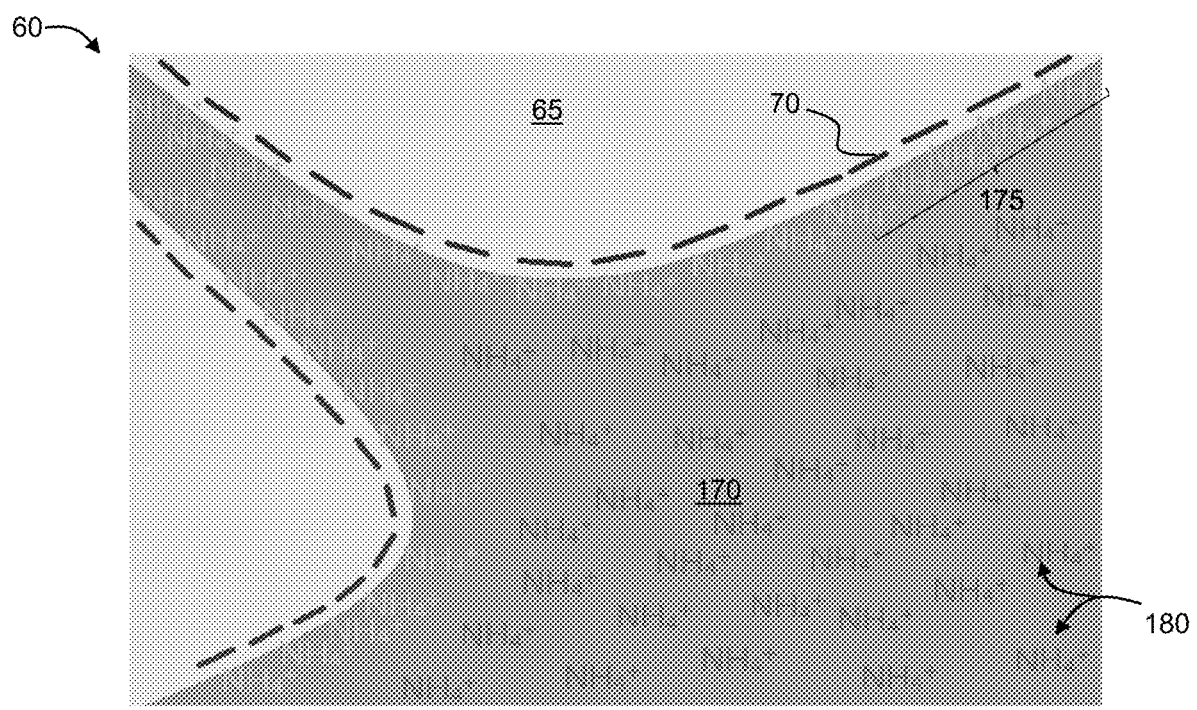

At this stage, the rock sample 60 may be coreflooded in order to remove the "total" exchangeable cations 155 from the sample 60 in order to quantify the total amount of exchangeable cations adsorbed to exchange sites 70. Such quantification may occur by displacement of the exchangeable cations 155 (as well as organic solvent 165) from the rock sample with a second injection fluid 170, the effect of which is shown in FIG. 8. Injection fluid 170 may include a replacement cation 175, such as $NH_4^+$ adsorbed onto the exchange sites 70. Additionally, injection fluid 170 may also include excess replacement cations 180 that are not adsorbed onto the exchange sites 70, but which are present in the injection fluid 170. To ensure complete displacement of total exchangeable cations 155, the about 50-80 pore volumes of injection fluid 170 may be injected into rock sample 60. In one or more embodiments, the injection fluid 170 may be an ammonium acetate solution, having a concentration ranging from 0.5 to 2.0M and a pH ranging from 7 to 8.5. However, it is envisioned that other injection fluids such a solution of hexaaminecobalt (III) chloride may also be used.

From the extract collected from the coreflooding with the injection fluid 170, the amount/concentration of the total exchangeable cations (those cations 155 that are adsorbed to all exchange sites 70, e.g., $Na^+$, $K^+$, $Ca^{2+}$ and $Mg^{2+}$) in the injection fluid extract may be determined by analytical methods, such as but not limited to ion chromatography (IC) specifically cation chromatography, atomic spectroscopic methods such as atomic absorption spectroscopy (AAS), inductively coupled plasma-mass spectrometry (ICP-MS), atomic emission spectrometry (ICP-AES), and optical emission spectrometry (ICP-OES), as well as capillary electrophoresis (CE). In one or more embodiments, the total amount of indigenous exchangeable cations may be considered as a mole equivalent per liter of pore volume and represented as $[NaX]_T$, $[KX]_T$, $[CaX_2]_T$, and $[MgX_2]_T$.

Depending on whether the wettability of each exchange site and/or the amount of each site occupied by crude oil is to be determined, a series of calculations may be performed using $[NaX]_e$, $[KX]_e$, $[CaX_2]_e$, and $[MgX_2]_e$ and $[NaX]_T$, $[KX]_T$, $[CaX_2]_T$, and $[MgX_2]_T$.

In one or more embodiments, the wettability of $Na^+$, $K^+$, $Ca^{2+}$, and $Mg^{2+}$ exchange sites may be determined. The wettability of each of $Na^+$, $K^+$, $Ca^{2+}$, and $Mg^{2+}$ exchange sites may be represented by $W_{NaX}$, $W_{KX}$, $W_{CaX_2}$, and $W_{MgX_2}$ and the following equations (1)-(4):

$$W_{NaX} = \frac{[NaX]_T - [NaX]_e}{[NaX]_T} \quad (1)$$

$$W_{KX} = \frac{[KX]_T - [KX]_e}{[KX]_T} \quad (2)$$

$$W_{CaX_2} = \frac{[CaX_2]_T - [CaX_2]_e}{[CaX_2]_T} \quad (3)$$

$$W_{MgX_2} = \frac{[MgX_2]_T - [MgX_2]_e}{[MgX_2]_T} \quad (4)$$

where a value of W=1 means the exchange site is completely oil-wet, and a value of W=0 means the exchange site is completely water-wet. Further, as is apparent, the wettability is calculated for each different exchange site present in the rock core sample.

In one or more embodiments, which of $Na^+$, $K^+$, $Ca^{2+}$, and $Mg^{2+}$ exchange sites are occupied by crude oil may be determined. The amount (in mole equivalent per liter of pore volume) of the $Na^+$, $K^+$, $Ca^{2+}$, and $Mg^{2+}$ exchange sites that are occupied by crude oil may be represented by $[NaX]_O$, $[KX]_O$, $[CaX_2]_O$, and $[MgX_2]_O$ and the following equations (5)-(8):

$$[NaX]_O = [NaX]_T - [NaX]_e \quad (5)$$

$$[KX]_O = [KX]_T - [KX]_e \quad (6)$$

$$[CaX_2]_O = [CaX_2]_T - [CaX_2]_e, \quad (7)$$

$$[MgX_2]_O = [MgX_2]_T - [MgX_2]_e, \quad (8)$$

Advantageously, the methods of the present application may provide for determinations concerning cation exchange sites in a rock sample, specifically, wettability and/or which are occupied by crude oil, in a manner that differentiates between different cation exchange sites, such as $Na^+$, $K^+$, $Ca^{2+}$, and $Mg^{2+}$. Using such determinations, an enhanced oil recovery operation may be better designed, for example, in terms of the compositional components included in an EOR injection fluid, whether in water flooding, or chemical flooding such as surfactant flooding, polymer flooding, alkaline/surfactant/polymer flooding, or reservoir preflushes for the chemical flooding processes, or the like.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A method for determining properties of different cation exchange sites in a rock core sample, at a preserved state of the rock core sample, the method comprising:
   providing a rock core sample that includes a plurality of indigenous exchangeable cations adsorbed onto the cation exchange sites, a plurality of cation exchange sites occupied by a crude oil, and one or more fluids occupying pore spaces in the rock core sample;
   subjecting the rock core sample to a plurality of coreflooding steps, the plurality of coreflooding step displacing the plurality of indigenous exchangeable cations, the crude oil, and the one or more fluids in at least three separate coreflooding steps to render the rock core sample clean of native components;
   determining an amount of indigenous exchangeable cations adsorbed onto the cation exchange sites;
   subjecting the rock core sample clean of native components to a plurality of coreflooding steps to determine a total amount of exchangeable cations adsorbed onto the cation exchange sites when the rock core sample is clean of native components; and
   determining at least one property of different cation exchange sites in the rock core sample at the preserved state based on the amount of indigenous exchangeable cations and the total amount of exchangeable cations.

2. The method of claim 1, wherein the subjecting the rock core sample to a plurality of coreflooding steps comprises:
   displacing the crude oil in the rock core sample with a formation brine until oil ceases production;
   displacing an excess of cations present in a plurality of interstitial pore spaces of the rock core sample by using a first organic solvent;
   displacing the plurality of indigenous exchangeable cations from the cation exchange sites of the rock core sample with a first injection fluid until completion of extraction; and
   displacing the injection fluid by alternately injecting a second organic solvent and a third organic solvent, wherein the third organic solvent is the last injected to render the rock core sample clean of native components.

3. The method of claim 2, wherein the amount of indigenous exchangeable cations is quantified from an extract of the first injection fluid upon completion of extraction by an analytical method.

4. The method of claim 2, wherein the first injection fluid is an ammonium acetate solution.

5. The method of claim 2, wherein the first organic solvent is ethanol.

6. The method of claim 2, wherein the second organic solvent is toluene and the third organic solvent is methanol.

7. The method of claim 1, wherein the subjecting the rock core sample clean of native components to a plurality of coreflooding steps comprises:
   coreflooding the rock sample clean of native components with the formation brine such that the cations present in the formation brine adsorb onto the cation exchange sites and an excess of cations are present in the plurality of interstitial pore spaces of the rock core sample clean of native components;
   displacing the excess of cations present in a plurality of interstitial pore spaces of the rock core sample by using a fourth organic solvent; and
   displacing the cations adsorbed onto the cation exchange sites of the rock core sample with a second injection fluid until completion of extraction.

8. The method of claim 7, wherein the total amount of exchangeable cations is quantified from an extract of the second injection fluid upon completion of extraction by an analytical method.

9. The method of claim 7, wherein the second injection fluid is an ammonium acetate solution.

10. The method of claim 7, wherein the fourth organic solvent is ethanol.

11. The method of claim 1, further comprising: determining a pore volume of the rock core sample.

12. A method for determining an amount of different cation exchange sites occupied by crude oil in a rock core sample, at a preserved state of the rock core sample, the method comprising:
    providing a rock core sample that includes at least a plurality of indigenous exchangeable cations adsorbed onto the cation exchange sites and a plurality of cation exchange sites occupied by a crude oil;
    displacing the crude oil in the rock core sample with a formation brine until oil ceases production;
    displacing an excess of cations present in a plurality of interstitial pore spaces of the rock core sample by using a first organic solvent;
    displacing the plurality of indigenous exchangeable cations from the cation exchange sites of the rock core sample with a first injection fluid until completion of extraction;
    displacing the first injection fluid by alternately injecting a second organic solvent and a third organic solvent, wherein the third organic solvent is the last injected;
    displacing the third organic solvent with the formation brine such that the cations present in the formation brine adsorb onto the cation exchange sites;
    displacing the cations adsorbed onto the cation exchange sites of the rock core sample with a second injection fluid until completion of extraction;
    calculating an amount of indigenous exchangeable cations adsorbed onto the cation exchange sites and a total amount of the exchangeable cations adsorbed onto the cation exchange sites; and
    calculating the amount of the different cation exchange sites occupied by crude oil based on the amount of indigenous exchangeable cations adsorbed onto the cation exchange sites and the total amount of the exchangeable cations adsorbed onto the cation exchange sites.

13. The method of claim 12, further comprising
    after displacing the third organic solvent, displacing excess of cations present in a plurality of interstitial pore spaces of the rock core sample by using a fourth organic solvent.

14. The method of claim 12, wherein the amount of indigenous exchangeable cations and the total amount of exchangeable cations are quantified from extracts of the first injection fluid and second injection fluid upon completion of extraction by analytical methods.

15. The method of claim 12, further comprising: determining a pore volume of the rock core sample.

16. The method of claim 12, wherein the calculating the amount of different cation exchange sites occupied by crude oil uses equations (5)-(8):

$$[NaX]_O = [NaX]_T - [NaX]_e \quad (5)$$

$$[KX]_O = [KX]_T - [KX]_e \quad (6)$$

$$[CaX_2]_O = [CaX_2]_T - [CaX_2]_e, \quad (7)$$

$$[MgX_2]_O = [MgX_2]_T - [MgX_2]_e, \quad (8)$$

wherein $[NaX]_O$, $[KX]_O$, $[CaX_2]_O$, and $[MgX_2]_O$ represent $Na^+$, $K^+$, $Ca^{2+}$, and $Mg^{2+}$ exchange sites that are occupied by crude oil; $[NaX]_T$, $[KX]_T$, $[CaX_2]_T$, and $[MgX_2]_T$ represent the total amount of exchangeable cations of $Na^+$, $K^+$, $Ca^{2+}$, and $Mg^{2+}$ adsorbed onto cation exchange sites, and $[NaX]_e$, $[KX]_e$, $[CaX_2]_e$, and $[MgX_2]_e$ represent the amount of indigenous cations of $Na^+$, $K^+$, $Ca^{2+}$, and $Mg^{2+}$ adsorbed onto cation exchange sites.

17. A method for determining a wettability of different cation exchange sites of a rock sample, at a preserved state of the rock core sample, the method comprising:
providing a rock core sample that includes at least a plurality of indigenous exchangeable cations adsorbed onto the cation exchange sites and a plurality of cation exchange sites occupied by a crude oil;
displacing the crude oil in the rock core sample with a formation brine until oil ceases production;
displacing an excess of cations present in a plurality of interstitial pore spaces of the rock core sample by using a first organic solvent;
displacing a plurality of indigenous exchangeable cations from the cation exchange sites of the rock core sample with a first injection fluid until completion of extraction;
displacing the first injection fluid by alternately injecting a second organic solvent and a third organic solvent, wherein the third organic solvent is the last injected;
displacing the third organic solvent with the formation brine such that the cations present in the formation brine adsorb onto the cation exchange sites;
displacing the cations adsorbed onto the cation exchange sites of the rock core sample with a second injection fluid until completion of extraction;
calculating an amount of indigenous exchangeable cations adsorbed onto the cation exchange sites and a total amount of the exchangeable cations adsorbed onto the cation exchange sites; and
calculating the wettability of the different cation exchange sites based on the amount of indigenous exchangeable cations adsorbed onto the cation exchange sites and the total amount of the exchangeable cations adsorbed onto the cation exchange sites.

18. The method of claim 17, further comprising
after displacing the third organic solvent, displacing excess of cations present in a plurality of interstitial pore spaces of the rock core sample by using a fourth organic solvent.

19. The method of claim 17, wherein the amount of indigenous exchangeable cations and the total amount of exchangeable cations are quantified from extracts of the first injection fluid and second injection fluid upon completion of extraction by analytical methods.

20. The method of claim 17, further comprising: determining a pore volume of the rock core sample.

21. The method of claim 17, wherein the calculating the wettability of different cation exchange sites uses equations (1)-(4):

$$W_{NaX} = \frac{[NaX]_T - [NaX]_e}{[NaX]_T} \quad (1)$$

$$W_{KX} = \frac{[KX]_T - [KX]_e}{[KX]_T} \quad (2)$$

$$W_{CaX_2} = \frac{[CaX_2]_T - [CaX_2]_e}{[CaX_2]_T} \quad (3)$$

$$W_{MgX_2} = \frac{[MgX_2]_T - [MgX_2]_e}{[MgX_2]_T} \quad (4)$$

wherein $W_{NaX}$, $W_{KX}$, $W_{CaX2}$, and $W_{MgX2}$ represent wettability of $Na^+$, $K^+$, $Ca^{2+}$, and $Mg^{2+}$ exchange sites; $[NaX]_T$, $[KX]_T$, $[CaX_2]_T$, and $[MgX_2]_T$ represent the total amount of exchangeable cations of $Na^+$, $K^+$, $Ca^{2+}$, and $Mg^{2+}$ adsorbed onto cation exchange sites, and $[NaX]_e$, $[KX]_e$, $[CaX_2]_e$, and $[MgX_2]_e$ represent the amount of indigenous cations of $Na^+$, $K^+$, $Ca^{2+}$, and $Mg^{2+}$ adsorbed onto cation exchange sites.

* * * * *